(12) United States Patent
Calle et al.

(10) Patent No.: US 8,818,518 B1
(45) Date of Patent: Aug. 26, 2014

(54) RESTORING A PAST CONFIGURATION TO A SOUND PROCESSOR OF A COCHLEAR IMPLANT SYSTEM

(75) Inventors: Guillermo A. Calle, Moorpark, CA (US); Tracey Kruger, Valencia, CA (US)

(73) Assignee: Advanced Bionics AG, Zug (CH)

( * ) Notice: Subject to any disclaimer, the term of this patent is extended or adjusted under 35 U.S.C. 154(b) by 744 days.

(21) Appl. No.: 12/847,197

(22) Filed: Jul. 30, 2010

(51) Int. Cl.
*A61N 1/04* (2006.01)

(52) U.S. Cl.
USPC .......................................................... 607/57

(58) Field of Classification Search
None
See application file for complete search history.

(56) References Cited

U.S. PATENT DOCUMENTS

| | | | |
|---|---|---|---|
| 2003/0133578 A1* | 7/2003 | Durant | 381/60 |
| 2003/0149756 A1* | 8/2003 | Grieve et al. | 709/223 |
| 2005/0222873 A1* | 10/2005 | Nephin et al. | 705/2 |
| 2008/0082144 A1* | 4/2008 | Marcotte et al. | 607/60 |

* cited by examiner

*Primary Examiner* — Brian T Gedeon
*Assistant Examiner* — Ankit Tejani
(74) *Attorney, Agent, or Firm* — ALG Intellectual Property, LLC

(57) ABSTRACT

An exemplary method of restoring a past configuration to a sound processor includes a fitting subsystem maintaining a configuration history including data representative of one or more past configurations of a sound processor, displaying a graphical depiction of the configuration history in a graphical user interface, receiving user input requesting that a past configuration within the one or more past configurations of the sound processor be restored to the sound processor, and utilizing data representative of the past configuration in the configuration history to restore the past configuration to the sound processor. Corresponding methods and systems are also described.

11 Claims, 10 Drawing Sheets

RESTORING A PAST CONFIGURATION TO A SOUND PROCESSOR OF A COCHLEAR IMPLANT SYSTEM

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When an implantable cochlear device of a cochlear implant system is initially implanted in a patient, and during follow-up tests and checkups thereafter, it is usually necessary to fit the cochlear implant system to the patient. Fitting of a cochlear implant system to a patient is not an exact science but an ongoing trial-and-error-based iterative exercise that is largely dependent on the experience of and feedback provided by the patient. For example, in a fitting session, an audiologist or the like typically utilizes a fitting system to present various stimuli to the patient and relies on subjective feedback from the patient as to how such stimuli are perceived. Based on this process, the audiologist utilizes the fitting system to configure the cochlear implant system for operation.

It is not uncommon, however, for a patient to be unsatisfied with modifications made to a configuration of a cochlear implant system during a fitting session. For example, after trying out a current configuration for a period of time, a patient may feel that the current configuration is inferior to a previous configuration of the cochlear implant system. However, a configuration of a cochlear implant system is typically a complicated aggregation of sound processing programs and other settings that when considered in combination may produce any of a large number of permutations. Consequently, an audiologist using a conventional fitting system faces a difficult task when asked by a patient to restore a cochlear implant system to a previous configuration. Even if the audiologist has detailed notes of the previous configuration, the use of such notes to restore the cochlear implant system to the previous configuration is prone to error, time consuming, inconvenient, and/or potentially frustrating to the audiologist and/or the patient.

SUMMARY

An exemplary method of restoring a past configuration to a sound processor includes a cochlear implant fitting subsystem 1) maintaining a configuration history including data representative of one or more past configurations of a sound processor, 2) displaying a graphical depiction of the configuration history in a graphical user interface, 3) receiving user input requesting that a past configuration within the one or more past configurations of the sound processor be restored to the sound processor, and 4) utilizing data representative of the past configuration in the configuration history to restore the past configuration to the sound processor.

Another exemplary method of restoring a past configuration to a sound processor includes a cochlear implant fitting subsystem 1) maintaining a configuration history including data representative of one or more past configurations of a sound processor of a cochlear implant system, 2) displaying a graphical depiction of the configuration history in a graphical user interface, 3) displaying a graphical indicator of a current configuration of the sound processor together with the graphical depiction of the configuration history in the graphical user interface, 4) receiving user input requesting that a past configuration within the one or more past configurations of the sound processor be restored to the sound processor, the user input comprising a drag-and-drop operation from the graphical depiction of the configuration history to the graphical indicator of the current configuration of the sound processor in the graphical user interface, and 5) utilizing, in response to the request, data representative of the past configuration in the configuration history to restore the past configuration to the sound processor.

An exemplary system of restoring a past configuration to a sound processor includes a configuration history facility that maintains a configuration history including data representative of one or more past configurations of a sound processor of a cochlear implant system. The system further includes a user interface facility communicatively coupled to the configuration history facility and that displays a graphical depiction of the configuration history in a graphical user interface and receives, by way of the graphical user interface, user input requesting that a past configuration within the one or more past configurations of the sound processor be restored to the sound processor. The system further includes a fitting facility communicatively coupled to the configuration history facility and the user interface facility and that utilizes, in response to the request, data representative of the past configuration in the configuration history to direct a restoration of the past configuration to the sound processor.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 7-9 illustrate exemplary views of a graphical user interface ("GUI") that may be presented for display according to principles described herein.

DETAILED DESCRIPTION

Figure 1:
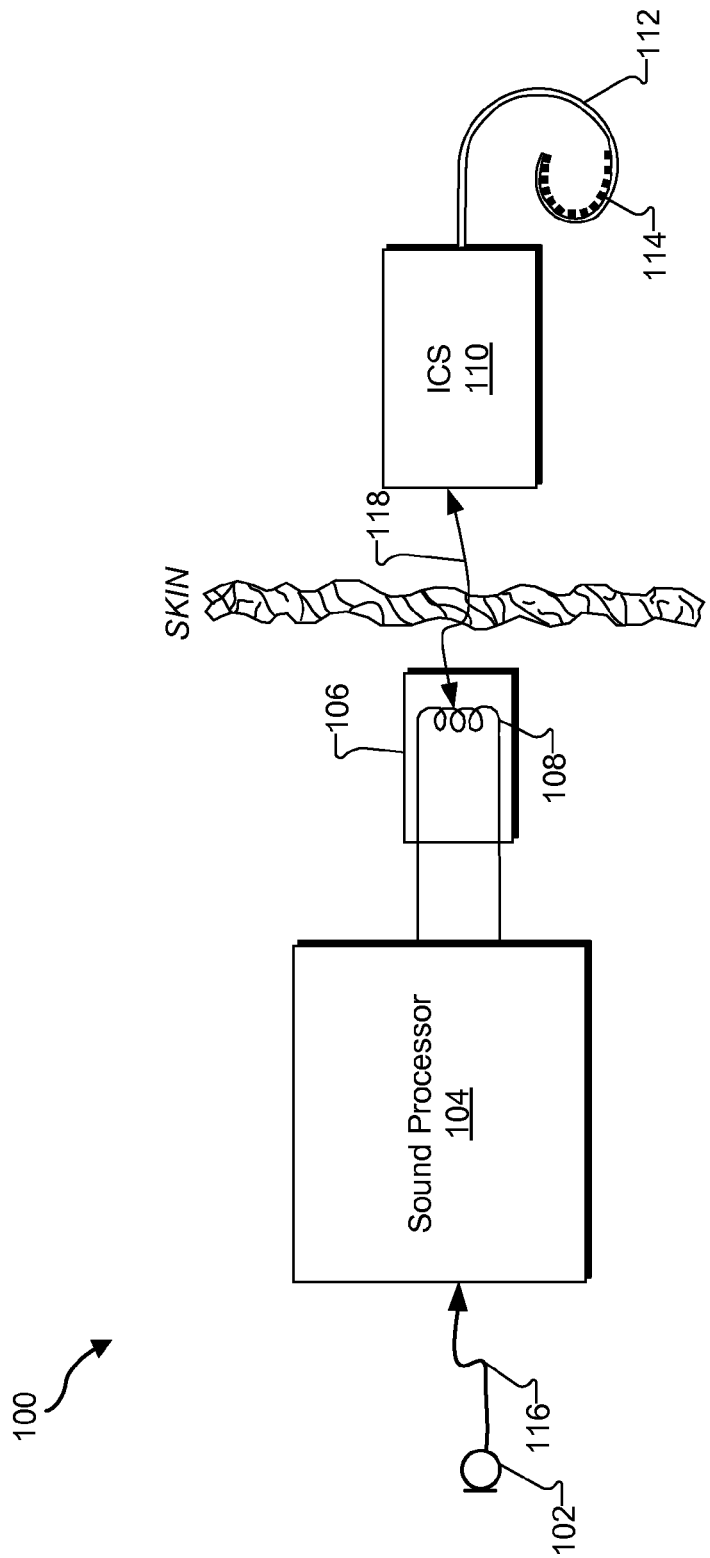
FIG. 1 illustrates an exemplary cochlear implant system according to principles described herein.

Methods and systems for restoring a past configuration to a sound processor of a cochlear implant system are described herein. As described in more detail below, a fitting subsystem may be configured to maintain a configuration history including data representative of one or more past configurations of a sound processor of a cochlear implant system, display a graphical depiction of the configuration history in a graphical user interface, receive user input requesting that a past configuration within the one or more past configurations of the sound processor be restored to the sound processor, and utilize data representative of the past configuration in the configuration history to restore the past configuration to the sound processor. In certain examples, the past configuration may include a configuration of one or more sound processing programs and/or one or more settings associated with the sound processing program(s) as previously loaded on the sound processor at a given time.

As used herein, the term "sound processing program" refers to any program that is executable by a sound processor included in a cochlear implant system. Hence, a sound processing program may specify a particular mode in which the sound processor is to operate. For example, a sound processing program may define a set of control parameters selected to optimize a listening experience of a cochlear implant patient in a particular listening environment (e.g., a relatively quiet room, a noisy restaurant, a musical environment, etc.). Other sound processing programs may be configured to facilitate measurement of one or more electrode impedances, performance of one or more neural response detection operations, and/or performance of one or more testing, diagnostic, and/or troubleshooting operations associated with the cochlear implant system. As will be described in more detail below, the fitting subsystem may adjust one or more control parameters associated with a particular sound processing program in response to patient feedback and/or user input in order to customize the sound processing program to the cochlear implant patient. The fitting subsystem may load (e.g., download) one or more sound processing programs and/or one or more settings associated with the sound processing program(s) to the sound processor, which may store the sound processing program(s) and/or setting(s) for use during normal operation of the cochlear implant system.

Numerous advantages may be associated with the methods and systems described herein. For example, by maintaining a configuration history of a sound processor of a cochlear implant system and utilizing the configuration history to restore a past configuration represented in the configuration history to the sound processor, the fitting subsystem may quickly and/or conveniently restore a past configuration of the sound processor without relying on an audiologist to manually record and/or use notes to restore the past configuration of the sound processor. In addition, fitting subsystem may provide an intuitive and convenient user interface, such as the exemplary graphical user interface ("GUI") views described herein, for use by a user of fitting subsystem to control restoration of a past configuration of the sound processor to the sound processor.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient, and implantable cochlear stimulator 110, lead 112, electrodes 114 may be implanted subcutaneously with the patient. In some alternative examples, microphone 102 and/or sound processor 104 may also be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing program loaded on sound processor 104 to generate appropriate stimulation parameters for controlling implantable cochlear stimulator 110. In certain examples, sound processor may 104 may include multiple sound processing programs loaded thereon such that a patient may select, from the multiple sound processing programs, which sound processing program to utilize to generate stimulation parameters. Accordingly, the patient may select a sound processing program that is well suited for a particular situation.

In certain examples, sound processing programs may be stored in slots within sound processor 104. As used herein, a "slot" is a logical concept associating a sound processing program and a set of control parameters with one of a plurality of program positions that may be selectable by a patient via a hardware switch disposed on sound processor 104. When a specific slot is selected, the sound processor locates the sound processing program for that slot, begins executing the located sound processing program, and points the executed sound processing program at the set of control parameters that are also associated with that slot.

Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter by which implantable cochlear stimulator 110 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 118. It will be understood that data communication link 118 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104, which stimulation parameters may be generated by sound processor 104 in accordance with a sound processing program loaded on the sound processor 104. Implantable cochlear stimulator 110 may be further configured to apply the electrical stimulation received from sound processor 104 to one or more stimulation sites within the cochlea via one or more electrodes 114 disposed along lead 112. In some examples, implantable cochlear stimulator 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
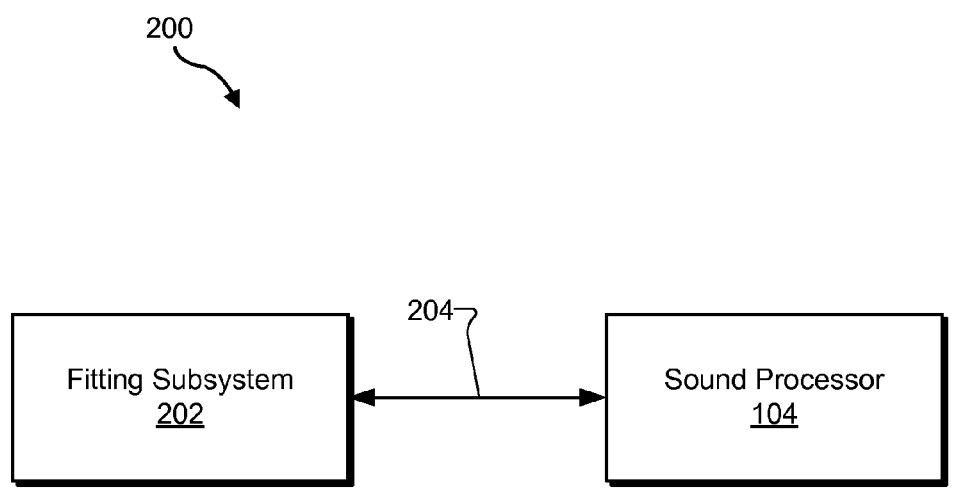
FIG. 2 illustrates an exemplary cochlear implant fitting system according to principles described herein.

FIG. 2 illustrates an exemplary cochlear implant fitting system 200 (or simply "fitting system 200") that may be used to fit cochlear implant system 100 to a patient. A fitting may include performance of one or more operations by fitting system 200 to fit sound processor 104 to the patient. As used herein, the terms "fitting a sound processor to a patient" and "fitting a cochlear implant system to a patient" will be used interchangeably to refer to performing one or more fitting operations associated with sound processor 104 and/or any other component of cochlear implant system 100. Such fitting operations may include, but are not limited to, adjusting one or more control parameters by which sound processor 104 and/or implantable cochlear stimulator 110 operate, measuring one or more electrode impedances, performing one or more neural response detection operations, performing one or more testing, diagnostic, and/or troubleshooting operations associated with the cochlear implant system, and loading, modifying, and/or deleting one or more sound processing programs on sound processor 104.

As shown in FIG. 2, fitting system 200 may include a fitting subsystem 202 configured to be selectively and communicatively coupled to sound processor 104 of cochlear implant system 100 by way of a communication link 204. Fitting system 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
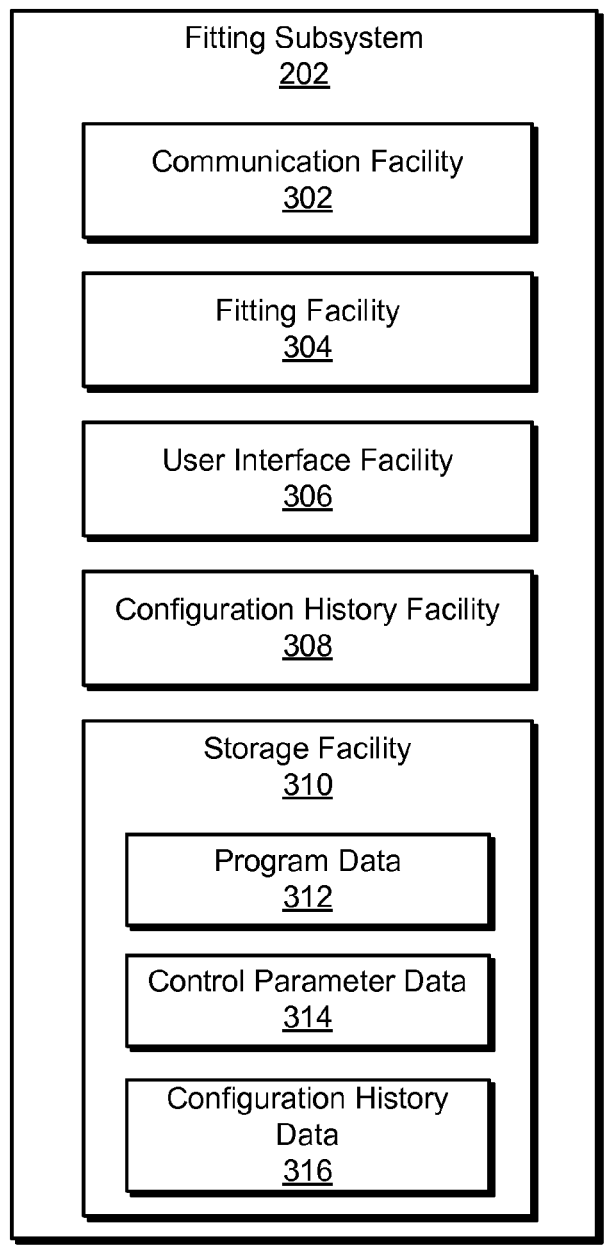
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a fitting facility 304, a user interface facility 306, a configuration history facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks).

Fitting facility 304 may be configured to perform one or more of the fitting operations described herein. For example, fitting facility 304 may be configured to adjust one or more control parameters by which sound processor 104 and/or implantable cochlear stimulator 110 operate, direct sound processor 104 to measure one or more electrode impedances, perform one or more neural response detection operations, and/or perform one or more testing, diagnostic, and/or troubleshooting operations associated with cochlear implant system 100.

In some examples, fitting facility 304 may be configured to direct a loading (e.g., a downloading) of one or more sound processing programs and/or associated control parameters onto sound processor 104. For example, fitting facility 304 may direct one or more components of fitting subsystem 202 to load a sound processing program and related control parameters into a slot of sound processor 104. As described in more detail further below, in some examples, the loading may include loading data representative of a past configuration of one or more sound processing programs and/or related control parameters onto sound processor 104 to restore the past configuration to sound processor 104. The loading may be performed in any suitable way.

Each time fitting facility 304 loads data onto sound processor 104, a configuration of sound processor 104 is modified. As used herein, the term "configuration of a sound processor" refers to a state of data loaded on a sound processor. Accordingly, a modification of a configuration of a sound processor may refer to any change in the state of data loaded on the sound processor. For example, when fitting facility 304 loads a new sound processing program and/or control parameters onto sound processor 104, the configuration of sound processor 104 is modified. The configuration of sound processor 104 may also be modified by fitting subsystem 202 deleting or otherwise modifying a sound processing program and/or control parameters loaded on sound processor 104.

User interface facility 306 may be configured to provide one or more user interfaces configured to facilitate user interaction with fitting subsystem 202. For example, user interface facility 306 may provide a GUI through which one or more functions, options, features, and/or tools associated with one or more operations described herein may be provided to a user and through which user input may be received. For example, a GUI may provide one or more functions, options, features, and/or tools related to a configuration history of a sound processor. For instance, a GUI may display a graphical depiction of a configuration history of a sound processor and may receive user input requesting that a past configuration within the configuration history be restored to the sound processor. Exemplary views of a configuration history GUI are described further below. In certain embodiments, user interface facility 306 may be configured to provide the GUI to a display device (e.g., a computer monitor) for display.

Configuration history facility 308 may be configured to maintain a configuration history of a sound processor. For example, configuration history facility 308 may maintain a configuration history including data representative of one or more past configurations of sound processor 104. Each past configuration in the configuration history may be associated with a particular time at which the configuration was loaded onto sound processor 104. Accordingly, each past configuration in the configuration history may represent a single time-stamped event associated with a modification of the configuration of sound processor 304.

In order to maintain a configuration history of sound processor 104, configuration history facility 308 may be configured to track modifications to the current configuration of sound processor 104. For example, configuration history facility 308 may be configured to detect one or more operations of fitting subsystem 202 that are indicative of a modification to the current configuration of sound processor 104, such as the receipt of designated user input commands and/or the sending of load, delete, or modification instructions from fitting subsystem 202 to sound processor 104.

In response to a detection of a modification of the current configuration of sound processor 104, configuration history facility 308 may determine and record data representative of a new configuration of sound processor 104. For example, configuration history facility 308 may determine that sound processor 104 is modified by a loading of a new sound processing program onto sound processor 104. Based on this determination, configuration history facility 308 may store data representative of the new configuration of sound processor 104 in the configuration history, such as by adding a new entry representative of the new configuration of sound processor 104 to the configuration history. The new entry may specify the new configuration of sound processor 104 (e.g., that the new sound processing program was loaded onto sound processor 104) and a time (e.g., date, timestamp, etc.) at which the new sound processing program was loaded onto sound processor 104.

Configuration history facility 308 may be further configured to generate and provide data representative of a configuration history of a sound processor to user interface facility 306 for use by user interface facility 306 in generating and displaying a GUI containing data representative of the configuration history. As mentioned, exemplary configuration history GUI views are described further below.

Configuration history facility 308 may be further configured to provide data representative of a past configuration of sound processor 104 to fitting facility 304 for use in restoring the past configuration of sound processor 104 to sound processor 104. Each entry in the configuration history may be self-contained such that fitting facility 304 may be able to rely exclusively on data received from configuration history facility 308 to restore a past configuration (including all associated parameters and/or settings) to sound processor 104.

Storage facility 310 may be configured to maintain program data 312 representative of one or more sound processing programs, control parameter data 314 representative of one or more control parameters, and configuration history data 316 representative of a configuration history of a sound processor of a cochlear implant system. Storage facility 310 may be configured to maintain additional or alternative data as may serve a particular implementation.

Figure 4:
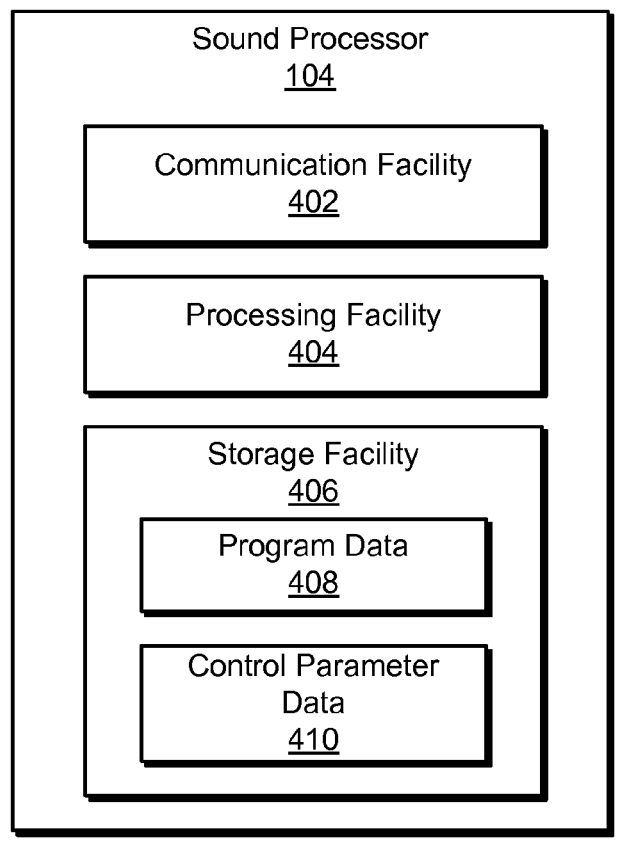
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and implantable cochlear stimulator 110. For example, communication facility 402 may include transceiver components configured to wirelessly transmit data (e.g., control parameters and/or power signals) to implantable cochlear stimulator 110 and/or wirelessly receive data from implantable cochlear stimulator 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of implantable cochlear stimulator 110 (e.g., one or more stimulation parameters defining the electrical stimulation to be generated and applied by implantable cochlear stimulator 110). Processing facility 404 may be configured to operate in accordance with one or more configurations of sound processing programs and/or control parameters loaded onto sound processor 104 by fitting subsystem 202 and/or otherwise stored within storage facility 406.

Storage facility 406 may be configured to maintain program data 408 representative of one or more sound processing programs (which, as described above, may be loaded onto sound processor 104) and control parameter data 410 representative of one or more control parameters. Program data 408 and/or control parameter data 410 may form a current configuration of sound processor 104. Storage facility 406 may be configured to maintain additional or alternative data as may serve a particular implementation.

Figure 5:
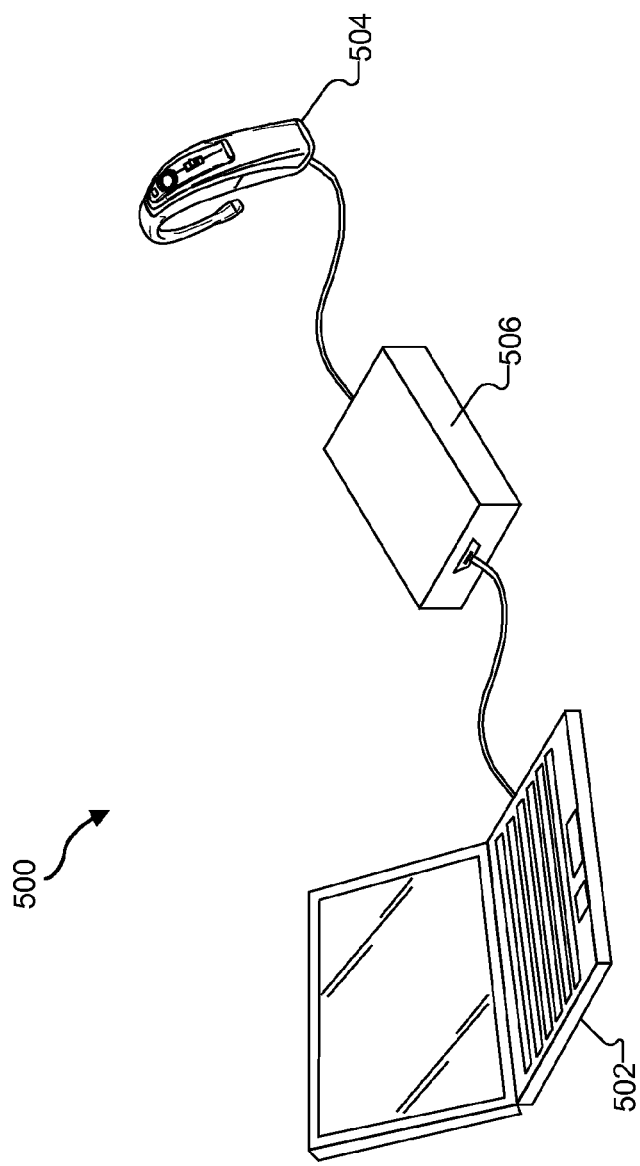
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor of a cochlear implant system as may serve a particular implementation.

Fitting station 502 may include any suitable computing device and/or combination of computing devices and be configured to perform one or more of the fitting operations described herein. For example, fitting station 502 may maintain a configuration history of BTE unit 504, display one or more configuration history GUIs configured to facilitate a restoration of a past configuration of BTE unit 504 to BTE unit 504, receive, by way of the one or more configuration history GUIs, user input requesting a restoration of a past configuration to BTE unit 504, and utilize the configuration history to restore the past configuration to BTE unit 504. Fitting station 502 may be utilized by an audiologist, a clinician, a product tester, a product manufacturer, and/or any other user to fit BTE unit 504 to a patient.

CPI device 506 may be configured to facilitate communication between fitting station 502 and sound processor 504. In some examples, CPI device 506 may be selectively and communicatively coupled to fitting station 502 and/or BTE unit 504 by way of one or more ports included within fitting station 502 and BTE unit 504.

Figure 6:
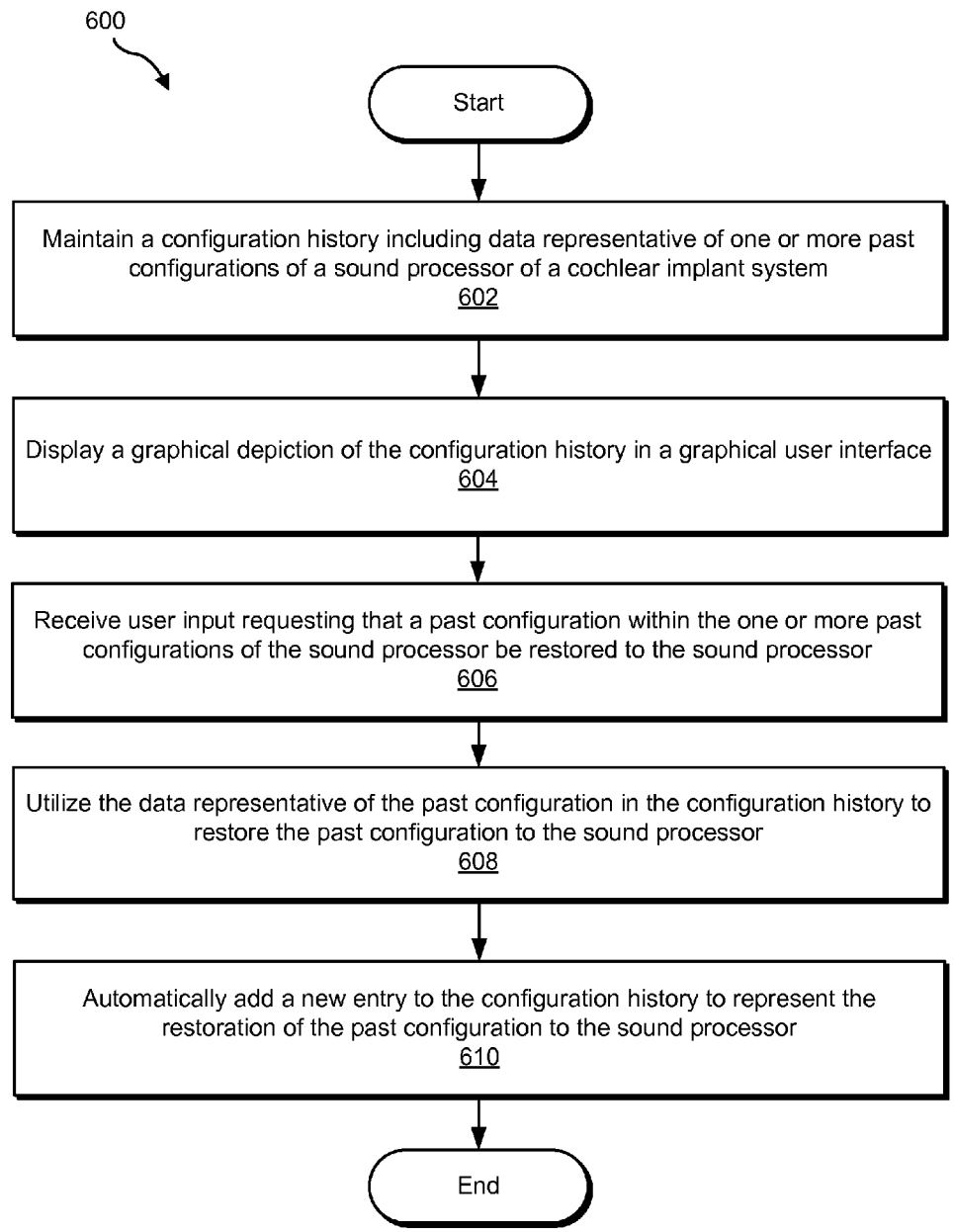
FIG. 6 illustrates an exemplary method of restoring a past configuration to a sound processor according to principles described herein.

FIG. 6 illustrates an exemplary method 600 of restoring a past configuration of a sound processor to the sound processor. While FIG. 6 illustrates exemplary steps according to one embodiment, other embodiments may omit, add to, reorder, combine, and/or modify any of the steps shown in FIG. 6. One or more of the steps shown in FIG. 6 may be performed by any component or combination of components of fitting subsystem 202 and/or fitting station 502.

In step 602, a configuration history including data representative of one or more past configurations of a sound processor of a cochlear implant system may be maintained. For example, fitting subsystem 202 may maintain a configuration history including data representative of one or more past configurations of sound processor 104. Data representative of the configuration history may be stored in any suitable form in storage facility 310 of fitting subsystem 202.

In step 604, a graphical depiction of the configuration history may be displayed in a GUI. For example, fitting subsystem 202 may display a graphical depiction of the configuration history in a GUI. Exemplary configuration history GUIs that may be displayed in step 604 are described further below in reference to FIGS. 7-9.

In step 606, user input requesting that a past configuration of the sound processor be restored to the sound processor may be received. For example, fitting subsystem 202 may receive user input requesting that a past configuration within the configuration history be restored to sound processor 104. In certain examples, the user input may be received by way of the GUI displayed in step 604.

In step 608, data representative of the past configuration in the configuration history may be utilized to restore the past configuration to the sound processor. For example, fitting subsystem 202 may utilize the data representative of the past configuration requested in step 606 to restore the past configuration to sound processor 104. Step 606 may be performed in any suitable way, including in any of the ways described herein. For instance, fitting subsystem 202 may load data representative of the past configuration onto sound processor 104 such that a restoration of the past configuration to sound processor 104 is accomplished.

In step 610, a new entry may be automatically added to the configuration history to represent the restoration of the past configuration to the sound processor. For example, fitting subsystem 202 may automatically add a new entry to the configuration history maintained in step 602. The new entry may represent the restoration of the past configuration to sound processor 104 performed in step 608. Although step 610 is shown as a separate step in FIG. 6, in certain embodiments, step 610 may be combined as part of step 602.

Figure 7:
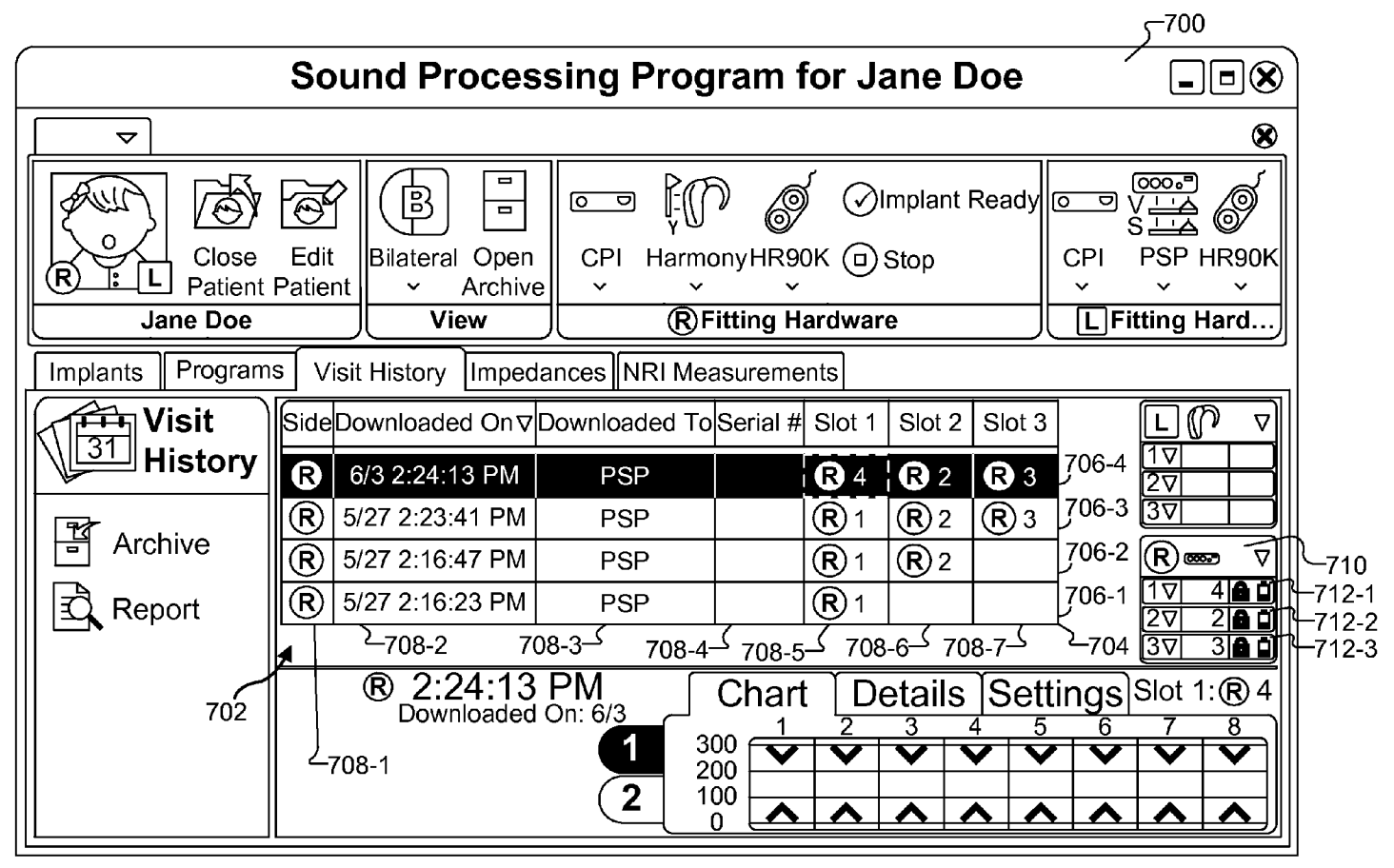
Figure 8:
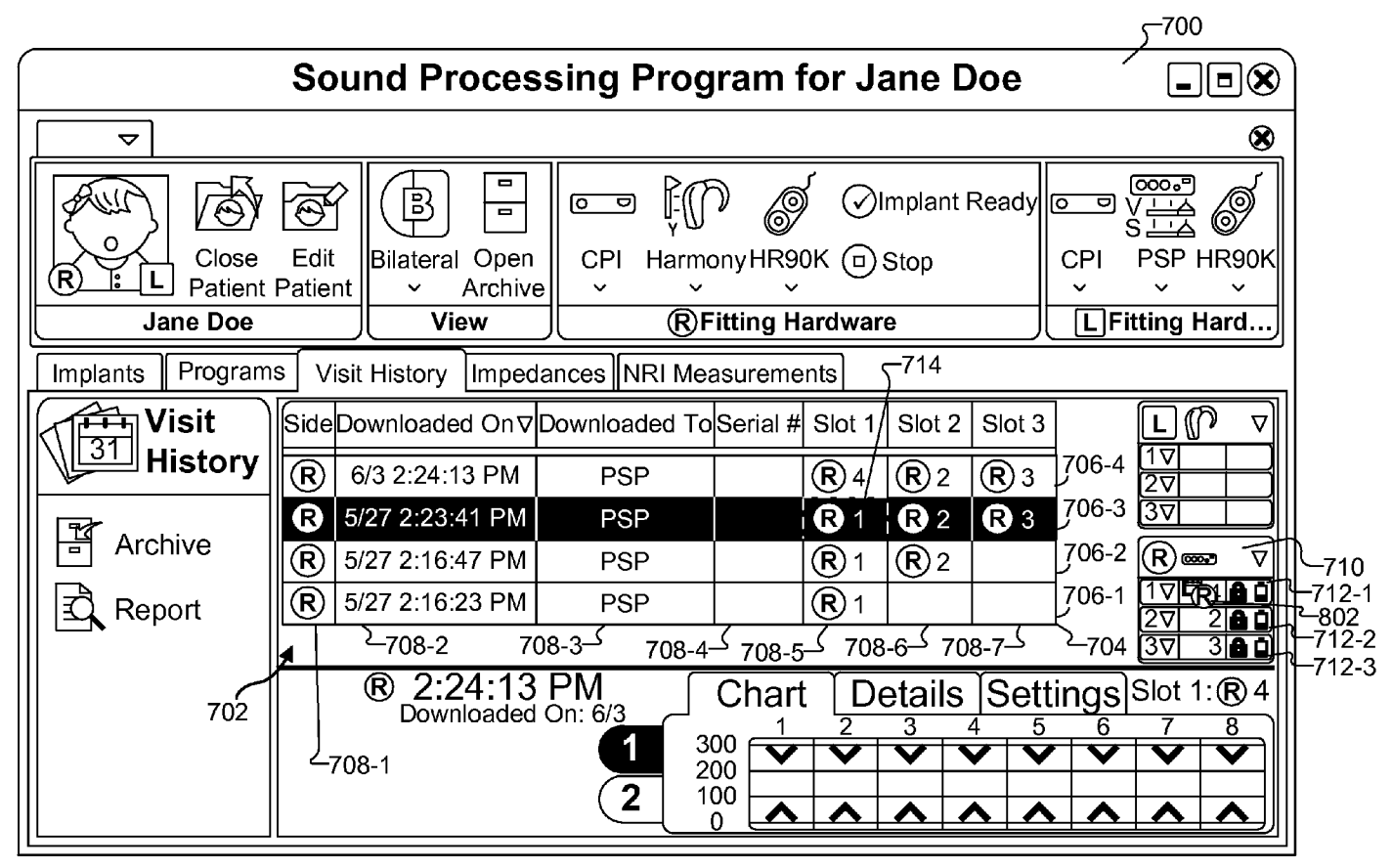
Figure 9:
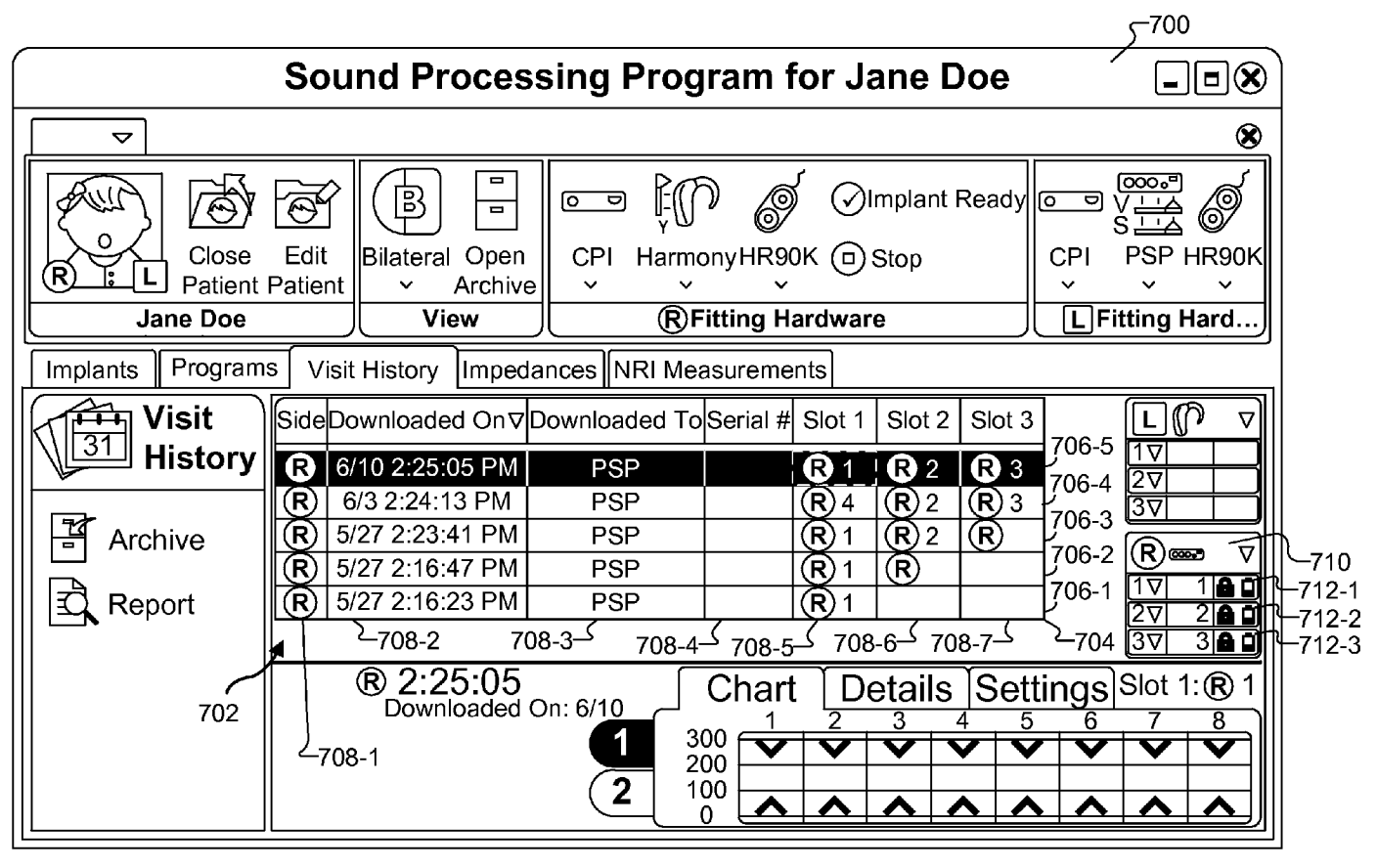

To further facilitate an understanding of exemplary methods and systems described herein, several exemplary GUI views will not be described in reference to FIGS. 7-9. FIG. 7 illustrates an exemplary GUI 700 including a configuration history view 702 displayed therein. GUI 700 may include graphical indicators representative of one or more past configurations of a sound processor identified as "PSP" in GUI 700. In addition, GUI 700 may include one or more graphical indicators representing the sound processor and/or a current configuration of the sound processor.

To illustrate, FIG. 7 shows GUI 700 to include a table 704 comprising data representative of a configuration history of the sound processor. Table 704 may include one or more graphical indicators representative of one or more past configurations of the sound processor. For example, table 704 may include a plurality of rows 706 (e.g., rows 706-1 through 706-4) representing past configurations of the sound processor. In certain examples, each of the rows 706 may be a graphical indicator representing a past configuration of the sound processor as a whole at a given time. In FIG. 7, the rows 706 are arranged in chronological order from bottom to top in GUI 700 based on the times at which the past configurations represented by the rows 706 were loaded on the sound processor. For example, row 706-1 indicates that a first sound processing program ("program 1") was loaded into a first slot ("slot 1") of the sound processor at 2:16:23 p.m. on May 27$^{th}$, a second sound processing program ("program 2") was loaded into a second slot ("slot 2") of the sound processor at 2:16:37 p.m. on May 27$^{th}$, a third sound processing program ("program 3") was loaded into a third slot ("slot 3") of the sound processor at 2:23:41 p.m. on May 27$^{th}$, and a fourth sound processing program ("program 4") was loaded into a first slot ("slot 1") of the sound processor to replace the first sound processing program ("program 1") at 2:24:13 p.m. on June 3$^{rd}$.

The programs may have been loaded onto the sound processor at fitting sessions performed during patient visits with a clinician. For example, during a visit of a patient to a clinic on May 27$^{th}$, an audiologist may have utilized fitting subsystem 202 to load "program 1," "program 2," and "program 3" onto the sound processor at the times respectively indicated in GUI 700. Subsequently, during another visit of the patient to the clinic on June 3$^{rd}$, the audiologist may have utilized fitting subsystem 202 to load "program 4" onto the sound processor to replace "program 1."

As shown in FIG. 7, table 704 may include data indicating a past configuration for each slot within the sound processor. To illustrate, table 704 may include a plurality of columns 708 (e.g., columns 708-1 through 708-7) depicting different information associated with past configurations of the sound processor. For example, column 708-1 may indicate a particular side (e.g., right or left ear) to which the sound processor is assigned, column 708-2 may include time entries indicating times at which past configurations were loaded onto the sound processor, column 708-3 may indicate type or name for the sound processor onto which the past configurations were loaded, column 708-4 may indicate a unique identifier for the sound processor onto which the past configurations were loaded, column 708-5 may indicate past configurations for a first slot ("slot 1") within the sound processor, column 708-6 may indicate past configurations for a second slot ("slot 2") within the sound processor, and column 708-7 may indicate past configurations for a third slot ("slot 7") within the sound processor. In particular, entries in a column associated with a slot within the sound processor may indicate sound processing programs that were previously loaded into the slot of the sound processor at given times.

In addition to graphical indicators of past configurations of the sound processor, GUI 700 may include one or more graphical indicators representing a current configuration of the sound processor. To illustrate, FIG. 7 shows GUI 700 to include a graphical indicator 710 representing the sound processor. As shown, graphical indicator 710 may depict a current configuration of the sound processor as a whole and/or for each slot within the sound processor. In the illustrated example, graphical indicator 710 indicates that three slots are defined within the sound processor, as well as the current configuration within each of the slots. For example, graphical indicator 710 indicates that a first slot 712-1 within the sound processor is configured with the fourth sound processing program ("program 4"), a second slot 712-2 within the sound processor is configured with the second sound processing program ("program 2"), and a third slot 712-3 within the sound processor is configured with the third sound processing program ("program 3").

As mentioned, fitting subsystem 202 may be configured to receive a request to restore a past configuration to the sound processor. The request may be received by way of GUI 700. For example, after the above-mentioned clinic visit on June 3$^{rd}$, the patient may decide that she prefers the previous configuration of the sound processor represented by row 706-3 in FIG. 7 over the current configuration of the sound processor represented by graphical indicator 710 in FIG. 7. That is, the patient may prefer to have the first sound processing program ("program 1") in the first slot ("slot 1") of the sound processor instead of the fourth sound processing program ("program 4"). During the next visit to the clinic, the patient may indicate her preference to the audiologist. In response, the audiologist may utilize fitting subsystem 202 to access and view the configuration history view 702 of GUI 700 shown in FIG. 7.

To illustrate, with configuration history view 702 displayed as shown in FIG. 7, the audiologist may provide user input by way of GUI 700 to request that the past configuration of the sound processor represented by row 706-3 be restored to the sound processor. The user input may be provided in any suitable way. In certain embodiments, for example, fitting subsystem 202 may provide a drag-and-drop tool configured to allow the audiologist to conveniently select and drag a graphical indicator representing the past configuration of the sound processor onto the graphical indicator 710 representing the sound processor to provide input requesting that the past configuration be restored to the sound processor. The drag-and-drop operation may be configured to request a restoration of a past configuration as a whole to the sound processor. For example, the audiologist may select and drag a row 706 of table 704 onto the graphical indicator 710 representing the sound processor in order to request that the past configuration associated with the row 706 be restored to the sound processor.

Additionally or alternatively, the drag-and-drop operation may be configured to request a restoration at a slot-specific level. For example, the audiologist may perform a drag-and-drop operation from a particular slot position within a graphical indicator representing a past configuration of the sound processor to a particular slot position within the graphical indicator 710 representing the current configuration of the sound processor. To illustrate, the audiologist may select and drag a cell of table 704 onto a slot position within the graphical indicator 710 representing a slot of the sound processor in order to request that the past configuration of the slot be restored to the slot of the sound processor. For instance, cell 714 may be dragged and dropped onto the first slot position of the graphical indicator 710 of the sound processor in order to request that the first program ("program 1") be restored to the first slot within the sound processor. FIG. 8 illustrates a drag-and-drop icon 802 representing a past configuration of the first slot of the sound processor being dragged from cell 714 and dropped onto the first slot position of the graphical indicator 710 representing the sound processor. As shown in FIG. 8, drag-and-drop icon 802 may comprise a calendar icon attached to a cursor icon. The user input requesting a restoration may be provided in any other way as may suit a particular implementation.

In response to the drag-and-drop operation (or other suitable user input requesting a restoration), data representative of the past configuration included in the configuration history may be utilized by fitting subsystem 202 to restore the past configuration to the sound processor. In the present example, for instance, the first program ("program 1") as it existed on the sound processor at 2:23:41 p.m. on May 27$^{th}$ may be loaded into the first slot ("slot 1") of the sound processor, effectively replacing the fourth program "program 4") as it existed on the sound processor at 2:24:13 p.m. on June 3$^{rd}$. In this or a similar manner, the graphical depiction of the configuration history of the sound processor may be utilized to conveniently restore a past configuration to the sound processor.

The configuration history may be updated to reflect the restoration. For example, a new entry may be added to the configuration history to represent the restored configuration of the sound processor. FIG. 9 illustrates a new entry added as a new row 706-5 in table 704. As shown, the row 706-5 may represent the restored configuration of the sound processor and the time (e.g., 2:25:03 p.m. on June 10$^{th}$) at which the restoration was performed.

In certain embodiments, fitting subsystem 202 may be configured to prevent cross-over restorations between left and right sound processors. For example, the past configurations depicted in GUI 700 represent past configurations of a sound processor assigned to the right ear of a patient. If an audiologist attempts to drag-and-drop a past configuration of a right-sided sound processor onto a sound processor assigned to the left ear of the patient, fitting subsystem 202 may detect the attempted cross-over, prevent the restoration from being performed, and/or notify the audiologist of the cross-over and the prevention thereof.

In certain embodiments, fitting subsystem 202 may be configured to search, filter, and/or sort information included in the configuration history and to display results of the search, filter, and/or sort operations in GUI 700. For example, table 704 may be searched, filtered, and/or sorted and the results displayed in GUI 700.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 10:
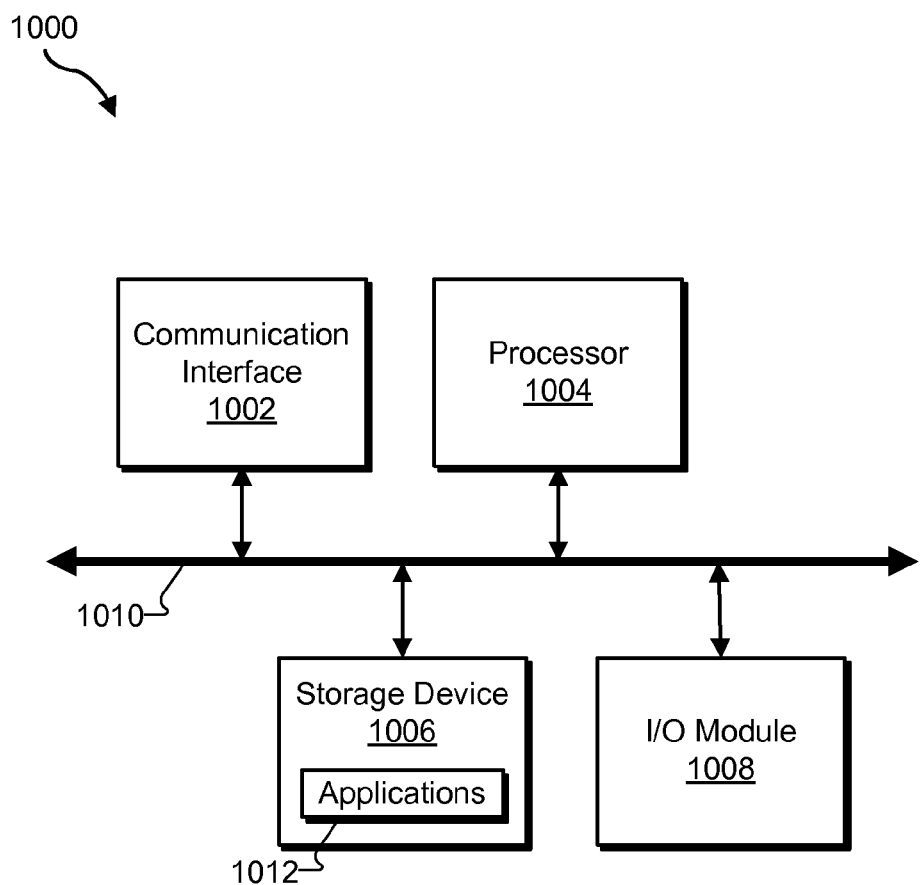
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, and any other suitable interface. Communication interface 1002 may additionally or alternatively provide such a connection through, for example, a local area network (such as an Ethernet network), a personal area network, a telephone or cable network, a satellite data connection, a dedicated URL, or any other suitable connection. Communication interface 1002 may be configured to interface with any suitable communication media, protocols, and formats, including any of those mentioned above.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another non-transitory computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 (which may include, but are not limited to, one or more of the software applications described herein) configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with communication facility 302, fitting facility 304, user interface facility 306, configuration history facility 308, communication facility 402, and/or processing facility 404. Likewise, storage facility 310 and/or storage facility 406 may be implemented by or within storage device 1006.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    maintaining, by a cochlear implant fitting subsystem, a configuration history including data representative of a plurality of past configurations of a sound processor of a cochlear implant system;
    displaying, by the cochlear implant fitting subsystem in a graphical user interface, a table that includes a plurality of rows representing each of the past configurations of the sound processor and a graphical depiction representing the sound processor, wherein
        a particular row in the table represents a past configuration included in the plurality of past configurations of the sound processor and identifies a plurality of different sound processing programs previously loaded in a plurality of slots within the sound processor during the past configuration, and
        the graphical depiction representing the sound processor includes a graphical indicator that represents a current configuration of the sound processor and that identifies one or more sound processing programs currently loaded into one or more of the plurality of slots within the sound processor during the current configuration;
    receiving, by the cochlear implant fitting subsystem via the graphical user interface, user input requesting that the past configuration as a whole be restored to the sound processor, the user input including a drag-and-drop operation in which a user drags the particular row to the graphical indicator included in the graphical depiction representing the sound processor; and
    utilizing, by the cochlear implant fitting subsystem in response to the user input, data representative of the past configuration to restore the past configuration to the sound processor by loading the plurality of previously loaded sound processing programs into the plurality of slots within the sound processor in place of the one or more currently loaded sound processing programs.

2. The method of claim 1, wherein:
    the graphical indicator representing the current configuration of the sound processor represents the current configuration of the sound processor as a whole.

3. The method of claim 1, further comprising automatically adding, by the cochlear implant fitting subsystem, a new entry to the configuration history to represent the restoration of the past configuration to the sound processor.

4. The method of claim 1, wherein:
    the configuration history includes data representative of one or more time entries respectively corresponding to the plurality of past configurations of the sound processor; and
    each time entry within the one or more time entries indicates a time at which a different past configuration within the plurality of past configurations was loaded onto the sound processor.

5. The method of claim 1, wherein the maintaining comprises:
    detecting a modification to the sound processor; and
    recording, in response to the detecting and based on the modification to the sound processor, data representative of a configuration of the sound processor in the configuration history.

6. The method of claim 1, embodied as computer-executable instructions on at least one non-transitory computer-readable medium.

7. A method comprising:
    maintaining, by a cochlear implant fitting subsystem, a configuration history including data representative of a plurality of past configurations of a sound processor of a cochlear implant system;
    displaying, by the cochlear implant fitting subsystem in a graphical user interface, a table that includes a plurality of rows representing each of the past configurations of the sound processor, a particular row in the table represents a past configuration included in the plurality of past configurations of the sound processor and identifies a plurality of different sound processing programs previously loaded in a plurality of slots within the sound processor during the past configuration;
    displaying, by the cochlear implant fitting subsystem, a graphical depiction of the sound processor together with the table in the graphical user interface, the graphical depiction of the sound processor including a graphical indicator that represents a current configuration of the sound processor and that identifies one or more sound processing programs currently loaded into one or more of the plurality of slots within the sound processor during the current configuration;
    receiving, by the cochlear implant fitting subsystem, user input requesting that the past configuration as a whole be restored to the sound processor, the user input comprising a drag-and-drop operation in which the user drags the particular row to the graphical indicator included in the graphical depiction representing the sound processor;
    utilizing, by the cochlear implant fitting subsystem in response to the user input, data representative of the past configuration in the configuration history to restore the past configuration to the sound processor by loading the plurality of previously loaded sound processing programs into the plurality of slots within the sound processor in place of the one or more currently loaded sound processing programs; and
    displaying, by the cochlear implant fitting subsystem in the graphical depiction of the sound processor and in response to the utilizing of the data to restore the past configuration to the sound processor, an additional graphical indicator indicating that the past configuration of the sound processor has been restored to the sound processor.

8. A system comprising:
a configuration history facility that maintains a configuration history including data representative of a plurality of past configurations of a sound processor of a cochlear implant system;
a user interface facility communicatively coupled to the configuration history facility and that
 displays, in a graphical user interface, a table that includes a plurality of rows representing each of the past configurations of the sound processor and a graphical depiction representing the sound processor, wherein
  a particular row in the table represents a past configuration included in the plurality of past configurations of the sound processor and identifies a plurality of different sound processing programs previously loaded in a plurality of slots within the sound processor during the past configuration, and
  the graphical depiction representing the sound processor includes a graphical indicator that represents a current configuration of the sound processor and that identifies one or more sound processing programs currently loaded into one or more of the plurality of slots within the sound processor during the current configuration, and
 receives, by way of the graphical user interface, user input requesting that the past configuration as a whole be restored to the sound processor, the user input including a drag-and-drop operation in which a user drags the particular row to the graphical indicator included in the graphical depiction representing the sound processor; and a fitting facility communicatively coupled to the configuration history facility and the user interface facility and that utilizes, in response to the user input, data representative of the past configuration in the configuration history to direct a restoration of the past configuration to the sound processor by loading the plurality of previously loaded sound processing programs into the plurality of slots within the sound processor in place of the one or more currently loaded sound processing programs.

9. The system of claim 8, wherein the configuration history facility is further configured to automatically add a new entry to the configuration history to represent the restoration of the past configuration to the sound processor.

10. The system of claim 8, wherein:
the configuration history includes data representative of one or more time entries respectively corresponding to the plurality of past configurations of the sound processor; and
each time entry within the one or more time entries indicates a time at which a different past configuration within the plurality of past configurations was loaded onto the sound processor.

11. The system of claim 8, wherein the configuration history facility maintains the configuration history by
detecting a modification to the sound processor, and
recording, in response to the detecting and based on the modification to the sound processor, data representative of a configuration of the sound processor in the configuration history.

* * * * *